United States Patent [19]
Shindo

[11] Patent Number: 5,262,807
[45] Date of Patent: Nov. 16, 1993

[54] EYE DIRECTION DETECTING APPARATUS
[75] Inventor: Osamu Shindo, Tokyo, Japan
[73] Assignee: Asahi Kogaku Kogyo Kabushiki Kaisha, Tokyo, Japan
[21] Appl. No.: 606,928
[22] Filed: Oct. 31, 1990
[30] Foreign Application Priority Data
Nov. 2, 1989 [JP]  Japan ................. 1-286854
[51] Int. Cl.⁵ .............................. A61B 3/00
[52] U.S. Cl. ................................. 351/210
[58] Field of Search ............... 351/209, 210, 246; 128/745

[56] References Cited
U.S. PATENT DOCUMENTS

| | | | |
|---|---|---|---|
| 4,735,498 | 4/1988 | Udden | 351/210 |
| 4,789,235 | 12/1988 | Borah | 351/246 |
| 4,836,670 | 6/1989 | Hutchinson | |
| 4,859,050 | 8/1989 | Borah | 351/210 |
| 4,958,925 | 9/1990 | Ober | 351/210 |

FOREIGN PATENT DOCUMENTS
3841575 7/1989 Fed. Rep. of Germany.

OTHER PUBLICATIONS
Copy of the German Office Action and English Language Translation.

Primary Examiner—Rodney B. Bovernick
Attorney, Agent, or Firm—Sandler, Greenblum & Bernstein

[57] ABSTRACT

An eye direction detecting apparatus having judgment zones in a view finder, each of which includes a focus detecting zone which corresponds to a focus detecting optical system. The apparatus detects a gaze point of a user's eye, judges which judgment zone includes the gaze point, and selects the focus detecting optical system corresponding to the selected zone in which the gaze point is located.

19 Claims, 6 Drawing Sheets

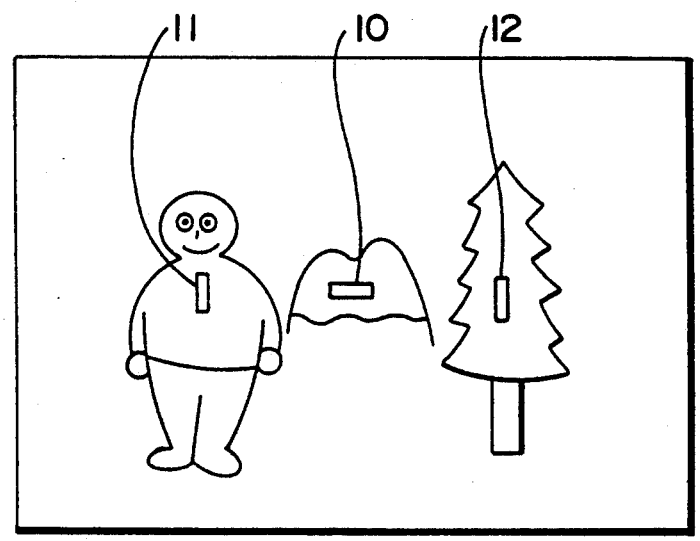

EYE DIRECTION DETECTING APPARATUS

BACKGROUND OF THE INVENTION

1. Field of the Invention

This invention relates to an eye direction detecting apparatus for finding an eye direction or gaze point of a user's eye in a finder system.

2. Description of the Prior Art

FIG. 9 shows a view finder of a conventional camera which has a multi-point focus detecting device. The camera has three focus detecting optical systems and three focus detecting zones 10, 11, 12 that correspond to a view of each focus detecting optical system in the view finder. Each of the focus detecting zones 10, 11, 12 indicate a scope of detection of each focus detecting optical system.

The camera has an eye direction detecting device (not shown), which finds a gaze point of the user's eye and judges which focus detecting zone the user looks at. The focus detecting zones coincide with the judgment zones used for judging a position of the gaze point.

When the gaze point is positioned in one of the focus detecting zones, the camera selects the focus detecting optical systems corresponding to the zone in which the gaze point is positioned. The camera detects a focus state of a taking lens with the selected focus detecting optical system, and makes the taking lens focus on the subject in the focus detecting zone. When the gaze point goes out from the focus detecting zone, the camera cancels the selection of the focus detecting optical system.

However, the conventional eye direction detecting apparatus is designed without considering a characteristic of the human's eye.

It is said that if an image is stationary in the same position on a retina, a visual sense is gradually lost away, and then the eye can not sense the image. In order to prevent such a loss of visual sense, the eye is usually moving. One motion is the so-called saccadic eye movement, which has an amplitude of 1 minute and a frequency of 30~80 cycles/sec. Also, another motion is the so-called drift, which is a slower random motion of the eye than the saccadic eye movement. Even if a man intends to look at one point, the eye of the man continuously moves.

In cases where the focus detecting zone coincides with the judgment zone, since the gaze point goes out of the judgment zone by an involuntary movement of gaze point, the selection and cancellation occurs very often. Furthermore, in cases where the user wears contact lenses, the contact lenses move whenever the user's eyes move, resulting in the detection of the gaze point dispersing.

SUMMARY OF THE INVENTION

The present invention has been accomplished in view of the above-mentioned problems. It is therefore an object of the present invention to provide an eye direction detecting apparatus which does not cancel the selection by an involuntary fine movement of the gaze point.

Another object is to provide an eye direction detecting apparatus which can make a stationary and accurate selection, even if a user wears contact lenses.

The eye direction detecting apparatus according to the present invention is characterized in that a judgment zone for judging the gaze point of the user's eye is formed more widely than the focus detecting zone in the finder.

BRIEF DESCRIPTION OF THE DRAWINGS

FIG. 9 is a schematic view of a view finder of a conventional camera which has a multi-point focus detecting optical system.

DETAILED DESCRIPTION OF THE EMBODIMENTS

The embodiment of the present invention will now be described with reference to the drawings. The present disclosure relates to subject matter contained in Japanese patent application No. HEI 1-286854 (filed on Nov. 2, 1989) which is expressly incorporated herein by reference in its entirety.

It should be noted that the expression "eye direction" used in this application means "the direction of a looking or viewing line of an eye", as a line being, of course, an imaginary one.

FIRST EMBODIMENT

Figure 1:
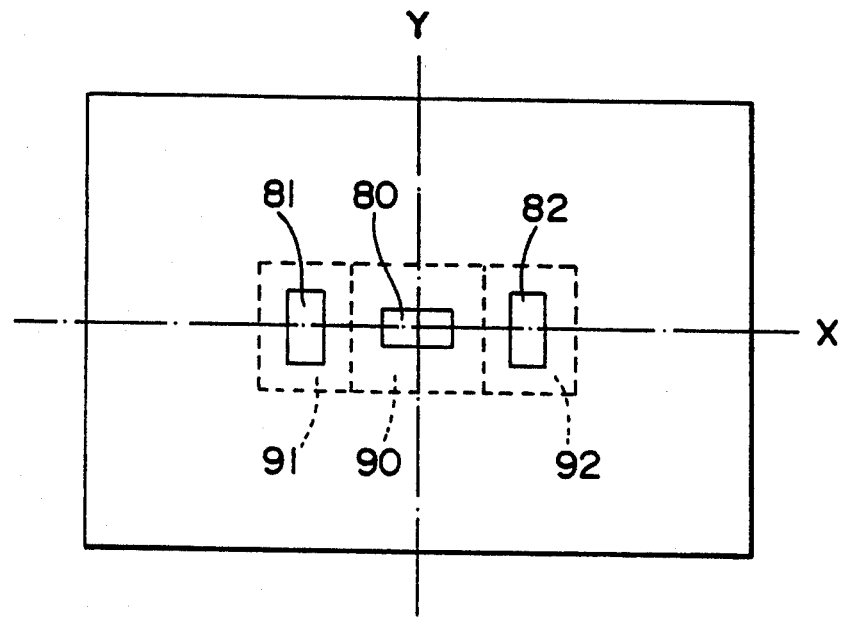
FIG. 1 is a schematic view of focus detecting zones and judgment zones in a view finder of the first embodiment according to the present invention.
Figure 2:
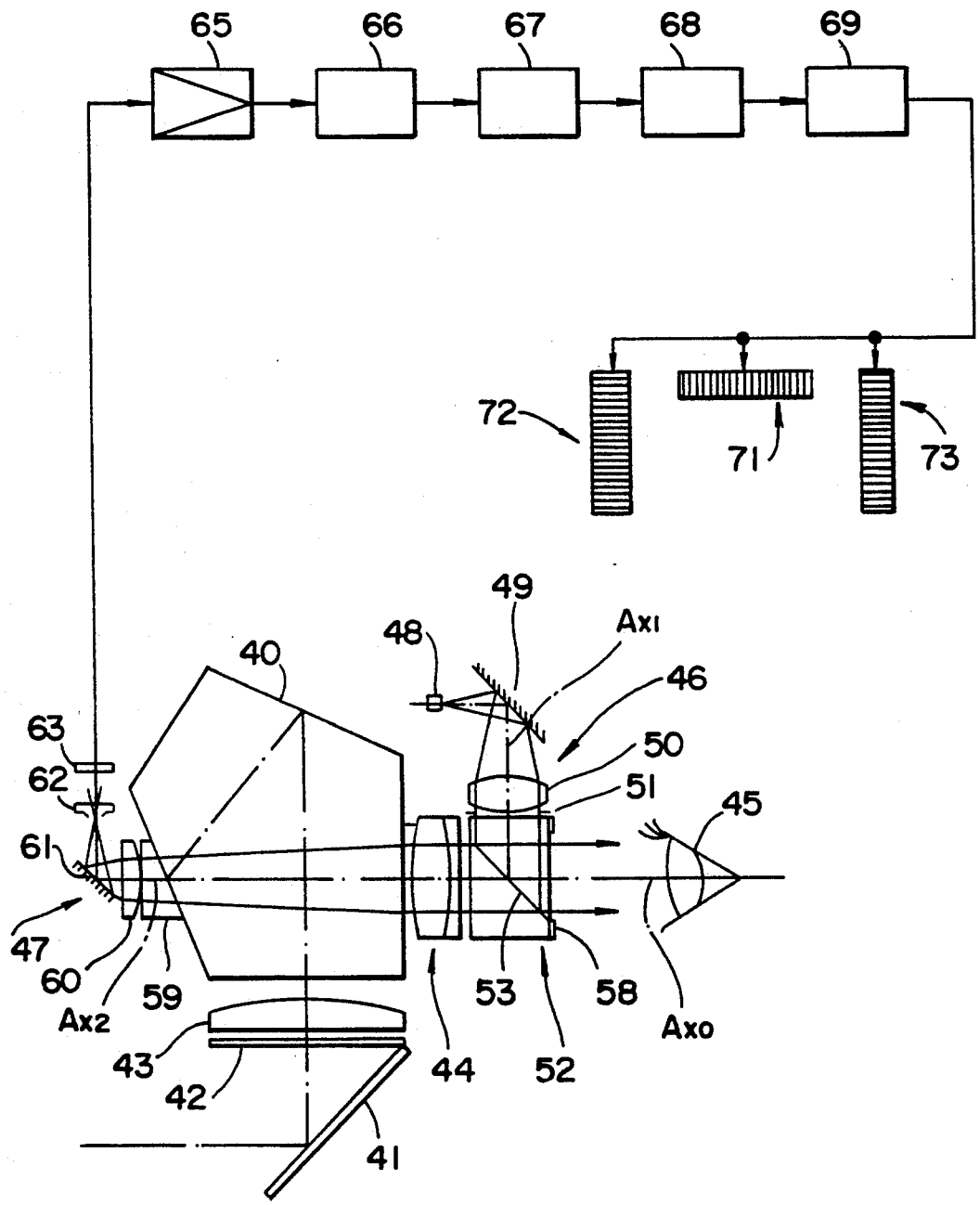
FIG. 2 is schematic view showing a general construction of the eye direction detecting device according to the first embodiment.

FIGS. 1 and 2 show a first embodiment of the present invention.

First, a construction of the apparatus is explained according to FIG. 2.

In FIG. 2, 40 denotes a pentagonal prism built in a camera, 41 a quick return mirror, 42 a focusing plate, 43 a condenser lens, 44 a finder eye piece lens, 45 an eye of the user, and AxO the optical axis of the finder system.

This camera is provided with three focus detecting optical systems(not shown), and each focus detecting optical system is provided with each of CCD line sensors 71, 72, 73.

As is shown in FIG. 1, three focus detecting zones 80, 81, 82 and three judgment zones 90, 91, 92 are located in the view finder. The focus detecting zones 80, 81, 82 correspond to a view of each of the focus detecting optical systems, and each judgment zone 90, 91, 92 includes each of the focus detecting zones. The judgment zones are arranged without a clearance between one another.

An eye direction detecting optical system has a light emitting system 46 and a light receiving system 47. The light emitting system 46 guides a parallel light beam to an eye of an user gazing into the finder. The light receiving system 47 detects light reflected by the eye.

The light emitting system 46 has an infrared light emitting diode 48, a total reflection mirror 49, and a collimator lens 50. An infrared light emitted from the light emitting diode 48 is reflected by the total reflection mirror 49 and is made incident into the collimator lens 50. The collimator lens 50 is provided at its outgoing side surface with a diaphragm 51. The collimator lens 50 functions to convert the infrared light emitted by the light emitting diode 48 into parallel pencil rays of light.

At the side of the finder eye piece lens 44 facing a user's eye 45, there is provided a light path overlapping optical member 52 for making the optical axis path of the light emitting system 46 and the optical path of the light receiving system 47 overlap. The light path overlapping optical member 52 comprises a rectangular parallelepiped comprising prisms 54 and 55 having a reflecting surface 53.

The reflecting surface 53 employed in this embodiment is the type for semi-transmitting an infrared light and for transmitting a visible light. Since the reflecting surface 53 transmits a visible light, the photographer can see an image of the object formed on a focusing plate 42. The parallel pencil rays of light passed through the diaphragm 51 are reflected by the reflecting surface 53 in the direction towards the eye 45 and are projected to the eye 45 of the photographer placed in an eye point.

A beam of light for forming a first Purkinje image, based on a corneal specular reflection of the eye 45 and reflecting light from a retina, transmit through the reflecting surface 53 of the light path overlapping optical member 52 and then guided to the light receiving system 47.

The light receiving system 47 comprises a compensator prism 59, a minifying lens 60, a total reflection mirror 61, a reimaging lens 62, and a CCD line sensor 63.

The user's eye 45 is usually placed on an eye point. The CCD line sensor 63 and the pupil of the user's eye 45 are optically conjugate with each other through the finder eye piece lens 44, the minifying lens 60, and the reimaging lens 62. The reflecting light from the eye 45 forms a silhouette of the pupil and the first Purkinje image on the CCD line sensor 63.

The output of the CCD line sensor 63 is amplified by the amplifier 65, then converted into a digital signal by an A/D converter 66. A digital output signal of the A/D converter 66 is inputted to a CPU 67 which acts as a judgment device and selecting device, and is then temporarily stored in a RAM 68.

The CPU 67 finds a distance "d" between a center of the pupil and the Purkinje image, and finds a revolving angle "$\theta$" based on a predetermined distance "k1" and the distance "d" according to the relation $\theta = \sin^{-1}(d/k1)$. The "k1" is a distance from the center of the pupil to a center curvature of the cornea.

The CPU 67 finds the coordinate (X,Y) of the gaze point at which the user gazes based on the revolving angle $\theta$, and judges which judgment zone the user looks at on the coordinate. In cases where the gaze point is positioned in any judgment zone, the CPU 67 judges that the user selects the focus detecting optical system corresponding to the judgment zone in which the gaze point is positioned. After the judgment, the CPU 67 output a selecting signal to a driving circuit 69.

The driving circuit 69 drives one of the CCD 71, 72, 73 which corresponds to the selected focus detecting optical system.

The focus detecting device (not shown) detects the focus state of the taking lens at a subject to be photographed. An automatic focusing device of the camera drives a taking lens to focus at the subject.

When the gaze point goes out from the judgment zone, the camera cancels the selection of the focus detecting optical system.

The apparatus of the first embodiment has the judgment zones being wider than the focus detecting zones, so that the apparatus does not excessively respond to an involuntary fine movement of the gaze point.

Figure 3:
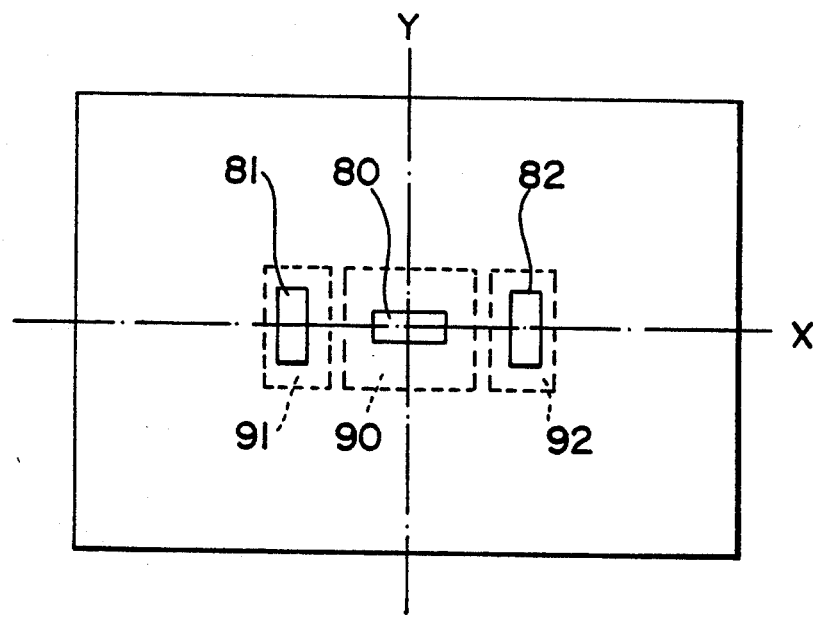
FIG. 3 is a schematic view of a variant example of the first embodiment.

FIG. 3 is a schematic view of a variant example of the first embodiment. In FIG. 3, each judgment zone is separately positioned with respect to one another. Each judgment zone is broader than each focus detecting zone. Therefore the judgment becomes stable, as in the variant shown in FIG. 1.

SECOND EMBODIMENT

Figure 4:
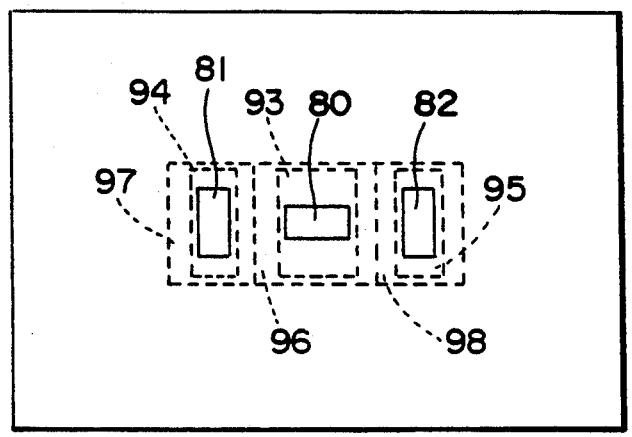
FIG. 4 is a schematic view of focus detecting zones and judgment zones in a view finder of the second embodiment according to the present invention.
Figure 5:
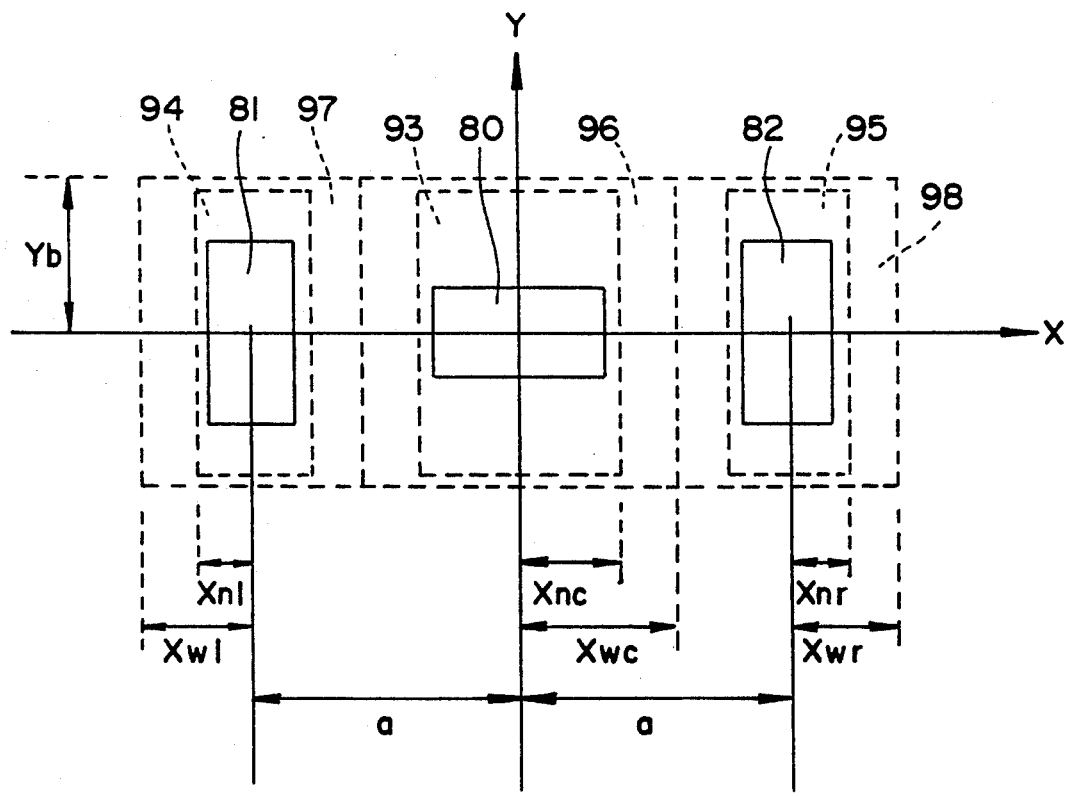
FIG. 5 is an enlarged view of FIG. 4.
Figure 6:
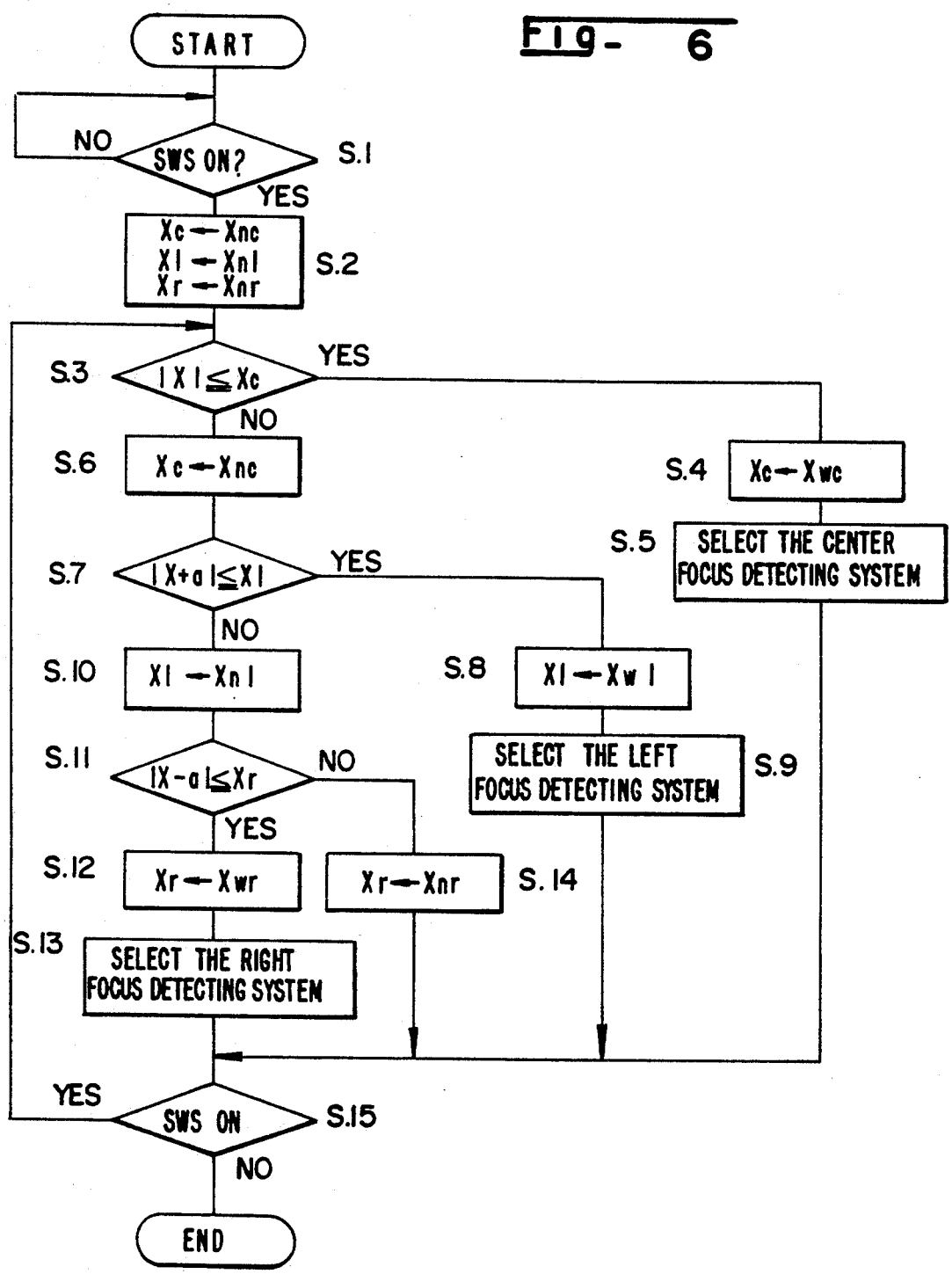
FIG. 6 is a flow chart showing a process of the second embodiment.

FIGS. 4 to 6 show a second embodiment of the present invention.

The second embodiment differs from the first embodiment with respect to the setting of the judgment zones and a method of selection. Only the different points will be explained.

The judgment zones of the second embodiment comprise two kinds of zones, as shown in FIGS. 4 and 5. One is inside judgment zones 93, 94, 95 which include each of focus detecting zones 80, 81, 82 and the other is outside judgment zones 96, 97, 98 which include each of the inside judgment zones. The outside judgment zones 96, 97, 98 are arranged without a clearance.

When the gaze point of the user's eye enters the inside judgment zone, the apparatus selects the focus detecting optical system corresponding to the inside judgment zone. After selection, if the gaze point shifts from the inside judgment zone, the selection is not canceled. When the gaze point goes out from the outside judgment zone, the selection is canceled. That is, when any focus detecting optical system is not selected, the judgment zone is narrow, and when one of the focus detecting optical system is selected, the judgment zone spreads in order not to cancel the selection by an involuntary fine movement of the gaze point.

CPU 67 executes the above mentioned functions according to a flow chart shown in FIG. 6. In this embodiment, a detection in an X axis direction is only explained. A Y axis detection can be executed by defining an area of the distance $\pm Yb$ from the origin as a judgment zone, connecting with the detection of the X axis direction.

In this embodiment, the reference character "Xnc" denotes a distance from the origin to a boundary of the central inside judgment zone 93, "Xwc" denotes a distance from the origin to a boundary of the central outside judgment zone 96, "a" denotes a distance from the origin to the center of the left focus detecting zone 81 or right focus detecting zone 82, "Xnl" denotes a distance from the center of the left focus detecting zone 81 to a boundary of the left inside judgment zone 97, "Xwl" denotes a distance from the center of the left focus detecting zone 81 to a boundary of the left outside judgment zone 97, "Xnr" denotes a distance from the center of the right focus detecting zone 82 to a boundary of the right inside judgment zone 95, and "Xwr" denotes a distance from the center of the right focus detecting zone 82 to a boundary of the right outside judgment zone 98.

Before the CPU 67 selects one of the focus detecting optical systems, the values of Xnc, Xnl, Xnr are substituted for variable Xc, Xl, Xr which define the area of each judgment zone. After the CPU selects one of the focus detecting optical systems, the values of Xwc, Xwl, Xwr are substituted for the variables Xc, Xl, Xr.

As shown in FIG. 6, the apparatus waits until a photometry switch SWS is switched ON in step 1. After the switch SWS is switched ON, the values of Xnc, Xnl, Xnr are substituted for variables Xc, Xl, Xr, which define the area of each judgment zone. In general, a camera has a photometry switch, which is set ON when a shutter button is depressed halfway, and a release switch, which is set ON when the shutter button is fully depressed. The selection of the focus detecting optical systems should be executed before the focus detecting, is executed, on the condition that the photometry switch is set ON.

In step 3, the CPU 67 determines whether the coordinate of the gaze point is positioned in the central judgment zone. If the gaze point is positioned in the central inside judgment zone 93, the judgment of step 3 is "Yes". If the gaze point is positioned in the outside central judgment zone 96 but is not in the inside zone 93, the determination of step 3 is "Yes" when Xc equals Xwc, but is "No" when Xc equals Xnc.

If the judgment of step 3 is Yes, the CPU substitutes Xwc for Xc in step 4 and outputs a signal, which indicates a selection of the central focus detecting optical system, to the driving circuit 69 in step 5.

If the judgment of the step 3 is "No", the CPU substitutes Xnc for Xc in step 6, and determines whether the gaze point is in the left judgment zone in step 7. If a is added to the X coordinate of the gaze point, a calculation can be executed under the condition that the origin is set at the center of the left focus detecting zone. If an absolute value of a added to the X coordinate of the gaze point is lower than Xl, it is able to judge that the gaze point is in the left judgment zone. If the gaze point is in the left judgment zone, the CPU substitutes Xwl for Xl in step 8, and the CPU outputs the selection signal, which indicates the selection of the left focus detecting optical system, to the driving circuit 69 in step 9.

If the gaze point is not positioned in any judgment zone, the left inside judgment zone is set as the left judgment zone in step 10, and the CPU determines whether the gaze point is positioned in the right judgment zone in step 11.

If the gaze point is positioned in the right judgment zone, the CPU sets the outside judgment zone as the right judgment zone in step 12. The CPU then substitutes Xwr for Xr and outputs the selection signal which indicates selection of the right focus detecting optical system, to the driving circuit 69 in step 13.

If the gaze point is not positioned in any judgment zone, the CPU substitutes Xnr for Xr in step 14. In step 15, if the photometry switch SWS is ON, the process returns to step 3.

If the photometry switch SWS is OFF, the process finishes.

The process after the selection of the focus detecting optical system is the same as the first embodiment.

In this embodiment, before and after the selection of the focus detecting optical system the width of the judgment zone is changed. Before the selection, the intention of the user can be judged accurately by the small zone. After the selection process, the apparatus can prevent the selected condition from being carelessly canceled by using the wide zone.

Figure 7:
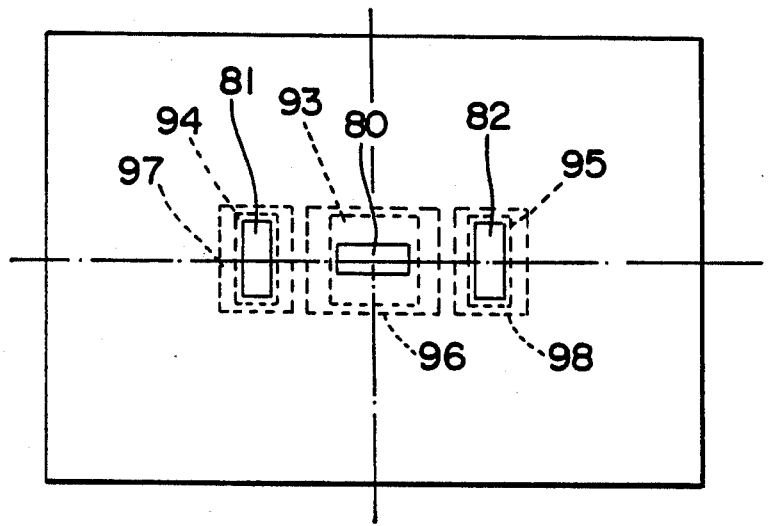
FIGS. 7 and 8 are schematic views of variant examples of the second embodiment.
Figure 8:
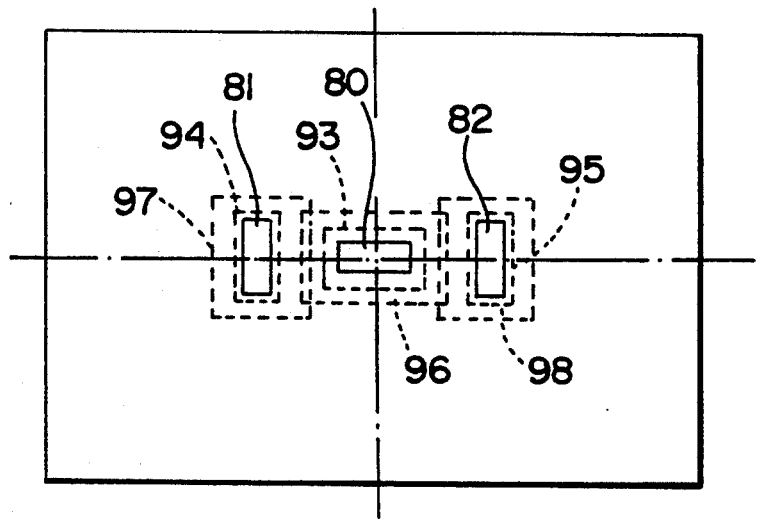

FIGS. 7 and 8 show variants of the second embodiment. In FIG. 7, each of the outside judgment zones 96, 97, 98 are separately positioned with one another. In FIG. 8, the outside judgment zone 96 overlaps with zones 97 and 98.

The invention in its broader aspects is not limited to the above embodiment, the selection of the focus detecting optical system. Additional advantages and modifications, such as a mode selection of the camera or a selection of proper values for shutter speed or aperture value, will readily occur to those skilled on the art.

What is claimed is:

1. An eye direction detecting apparatus, comprising:
    means for defining a plurality of focus detecting zones in a view finder, each of said focus detecting zones corresponding to a detecting area of a focus detecting optical system;
    means for defining a plurality of judgement zones, each of said judgement zones including one of said focus detecting zones;
    means for detecting a gaze point of a user's eye;
    means for determining which of said judgement zones includes said gaze point; and
    means for selecting one focus detecting optical system that corresponds to said judgement zone determined by said determining means to include said gaze point.

2. The apparatus according to claim 1, wherein said judgement zones are positioned in contacting relation with one another.

3. The apparatus according to claim 1, wherein said judgment zones are separately positioned from one another.

4. The apparatus according to claim 1, wherein said judgment zones partially overlap with one another.

5. The apparatus according to claim 1, wherein each of said detecting zones is smaller than said judgement zone including said detecting zone.

6. An eye direction detecting apparatus, comprising:
    means for defining a plurality of judgement zones that are positioned in contacting relation with one another in a view finder;
    means for detecting an eye direction so as to determine a gaze point of a user's eye; and
    means for determining which of said judgement zones includes said gaze point.

7. The apparatus according to claim 6, wherein said judgment zones include focus detecting zones set in said view finder that correspond to view fields of focus detecting optical systems.

8. An eye direction detecting apparatus, comprising:
    means for defining a plurality of judgement zones positioned in a view finder, said judgement zones partially overlapping one another;
    means for detecting an eye direction so as to determine a gaze point of a user's eye;
    means for determining which of said judgement zones includes said gaze point;
    selecting means for determining that a user selects one of said judgement zones when said gaze point enters into one of said judgement zones; and
    canceling means for determining that a user cancels the selection of said judgement zone when said gaze point goes out from said selected judgement zone.

9. The apparatus according to claim 8, wherein said judgement zones includes focus detecting zones set in said view finder that correspond to view fields of focus detecting optical systems.

10. An eye direction detecting apparatus comprising:

means for defining a plurality of inside judgement zones in a finder;
means for defining a plurality of outside judgement zones, each of said outside judgement zones including one of said inside judgement zones;
means for detecting an eye direction to detect a gaze point of a user's eye;
means for determining which of said judgement zones includes said gaze point;
selecting means for judging that a user selects one of said inside judgement zones when said gaze point enters into one of said inside judgement zones; and
canceling means for judging that a user cancels the selection of said judgement zone when said gaze point goes out from an outside judgement zone corresponding to said selected inside judgement zone.

11. The apparatus according to claim 10, wherein said outside judgement zones are separately positioned with respect to one another.

12. The apparatus according to claim 10, wherein said outside judgement zones are positioned in contacting relation with one another.

13. The apparatus according to claim 10, wherein said outside judgement zones are positioned so as to partially overlap with one another.

14. An eye direction detecting apparatus comprising:
means for defining a plurality of focus detecting zones in a view finder, each of said focus detecting zones corresponding to respective focus detecting optical systems;
means for defining a plurality of inside judgement zones, each of said inside judgement zones including a respective one of said focus detecting zones;
means for defining a plurality of outside judgement zones, each of said outside judgement zones including a respective one of said inside judgement zones;
means for detecting a gaze point of an user's eye;
selecting means for judging that a user selects one of said focus detecting optical systems when said gaze point enters into one of said inside judgement zones; and
canceling means for judging that a user cancels said selection of said focus detecting optical system when said gaze point goes out from said outside judgement zone corresponding to said selected focus detecting optical system.

15. An eye direction detecting apparatus comprising:
means for defining a plurality of judgement zones in a view finder;
means for detecting an eye direction and judging which of said judgement zones includes a gaze point of a user's eye; and
means for changing a width of said judgement zone.

16. The apparatus according to claim 15, further comprising:
selecting means for determining that a user selects one of said judgement zones when said judging means judges that said judgement zone includes said gaze point; and
canceling means for determining that a user cancels a selection of one of said judgement zones when said gaze point goes out from said selected judgement zone.

17. The apparatus according to claim 16, wherein when said selecting means determines that one of said judgement zones has been selected, said width changing means increases a width of said selected judgement zone.

18. The apparatus according to claim 16, wherein when said canceling means determines that the selection of one of said judgement zones has been canceled, said width changing means decreases a width of said canceled judgement zone.

19. An eye direction detecting apparatus comprising:
means for defining a plurality of judgement zones in a view finder;
means for detecting an eye direction to determine a gaze point of a user's eye; and
means for determining a selection of one of said judgement zones and for determining that said selection is canceled based on said gaze point detected by said detecting means.

* * * * *